US006063284A

United States Patent [19]
Grill

[11] Patent Number: 6,063,284
[45] Date of Patent: May 16, 2000

[54] SINGLE COLUMN CLOSED-LOOP RECYCLING WITH PERIODIC INTRA-PROFILE INJECTION

[75] Inventor: Charles M. Grill, Greenwich, R.I.

[73] Assignee: EM Industries, Inc., Hawthorne, N.Y.

[21] Appl. No.: 08/857,039

[22] Filed: May 15, 1997

[51] Int. Cl.[7] .................................................. B01D 15/08
[52] U.S. Cl. ...................................... 210/659; 210/198.2
[58] Field of Search .................................... 210/635, 656, 210/659, 198.2

[56] References Cited

U.S. PATENT DOCUMENTS

| | | | |
|---|---|---|---|
| 3,992,175 | 11/1976 | Klementi et al. | 55/67 |
| 4,001,112 | 1/1977 | Barker et al. | 210/31 C |
| 4,137,161 | 1/1979 | Shimada et al. | 210/31 |
| 4,267,054 | 5/1981 | Yoritomi et al. | 210/659 |
| 4,359,323 | 11/1982 | LePage | 23/230 M |
| 4,379,751 | 4/1983 | Yoritomi et al. | 210/659 |
| 4,412,866 | 11/1983 | Schoenrock et al. | 127/46.2 |
| 4,478,720 | 10/1984 | Perrut | 210/659 |
| 4,498,991 | 2/1985 | Oroskar | 210/659 |

(List continued on next page.)

FOREIGN PATENT DOCUMENTS

| | | | |
|---|---|---|---|
| 0 127 926 | 12/1984 | European Pat. Off. | 210/198.2 |
| 0 309 380 | 3/1989 | European Pat. Off. | 210/659 |

OTHER PUBLICATIONS

Snyder, Introduction to Modern Liquid Chromatography John Wiley & Sons, 1979, pp. 113–114.
Snyder, Introduction to Modern Liquid Chromatography John Wiley & Son, Inc. New York, 1979 pp. 519–522.
English Abstract—JP01165953A.
English Abstract—FR2527934.
Patent Abstracts of Japan, vol. 013, No. 436, pp. 938, Sep. 29, 1989, Hitachi Ltd.
Henry et al., "High Speed Recycle Chromatography Using an Alternate . . . ," *J. of Chromatographic Science*, vol. 12, pp. 197–199, Apr. 1974.
Broughton et al., "The Parex Process for Recovering Par-axylene", *Chem. Eng. Progress*, 66(9):70–75, Sep. 1970.
Bailly et al., "Recycle Optimization in Non–Linear Productive Chromatography–I", *Chemical Engineering Science*, 38(8):1199–1212, 1982.
Dingenen et al., "Preparation Chromatographic Resolution of Racemates on Chiral Stationary Phases on Laboratory and Production Scales by Closed–Loop Recycling Chromatography", *Journal of Chromatography A*, 666:627–650, 1994.
Porter et al., "Circular Gas Chromatograph", *Nature*, 4558:391–392, 1959.
Bailly et al., "Reversibility and Performances in Productive Chromatography", *Chem Eng Process* vol. 18, pp. 293–302 (1984).
Charton et al., "Recycling in preparative liquid chromatography", *J of Chromatography A*, vol. 687, pp. 13–31 (1994).

*Primary Examiner*—Ernest G. Therkorn
*Attorney, Agent, or Firm*—Millen, White, Zelano & Branigan, P.C.

[57] ABSTRACT

A preparative chromatographic cyclical process utilizing a single column comprising, at steady state: (a) establishing and maintaining a circulating chromatographic profile through said column and through one solvent pump; (b) discontinuously and periodically injecting a sample comprising at least two components, into the interior of said maintained circulating profile; and (c) collecting, discontinuously and periodically, at least two enriched fractions from said circulating profile.

4 Claims, 13 Drawing Sheets

U.S. PATENT DOCUMENTS

| | | | |
|---|---|---|---|
| 4,528,101 | 7/1985 | Burke et al. | 210/656 |
| 4,530,234 | 7/1985 | Cullick et al. | 73/53 |
| 4,536,199 | 8/1985 | Toon | 55/67 |
| 4,724,081 | 2/1988 | Kawahara | 210/659 |
| 4,840,730 | 6/1989 | Saxena | 210/198.2 |
| 4,919,595 | 4/1990 | Likuski et al. | 417/18 |
| 4,970,002 | 11/1990 | Ando et al. | 210/659 |
| 4,990,259 | 2/1991 | Kearney | 210/656 |
| 5,064,539 | 11/1991 | Tanimura | 210/659 |
| 5,071,547 | 12/1991 | Cazer et al. | 210/198.2 |
| 5,089,126 | 2/1992 | Silebi et al. | 210/192.2 |
| 5,093,004 | 3/1992 | Hotier et al. | 210/659 |
| 5,100,557 | 3/1992 | Nogami et al. | 210/656 |
| 5,108,466 | 4/1992 | Klein et al. | 55/20 |
| 5,114,590 | 5/1992 | Hotier et al. | 219/659 |
| 5,122,275 | 6/1992 | Rasche | 210/198.2 |
| 5,156,736 | 10/1992 | Schoenrock | 210/264 |
| 5,166,076 | 11/1992 | Müller et al. | 436/161 |
| 5,180,487 | 1/1993 | Saito et al. | 210/198.2 |
| 5,196,039 | 3/1993 | Phillips et al. | 55/67 |
| 5,253,981 | 10/1993 | Yang et al. | 417/3 |
| 5,384,035 | 1/1995 | Smolnik et al. | 210/635 |
| 5,393,420 | 2/1995 | Hutchins et al. | 210/198.2 |
| 5,393,434 | 2/1995 | Hutchins et al. | 210/656 |
| 5,398,539 | 3/1995 | Gordon et al. | 73/23.35 |
| 5,567,307 | 10/1996 | Karmarkar | 210/198.2 |
| 5,630,943 | 5/1997 | Grill | 210/659 |

SINGLE COLUMN CLOSED-LOOP RECYCLING WITH PERIODIC INTRA-PROFILE INJECTION

FIELD OF THE INVENTION

The invention relates to processes of performing preparative chromatography in an efficient, repetitive manner, and to apparatus therefor.

BACKGROUND OF THE INVENTION

Among the numerous proposed and utilized preparative chromatographic techniques are: (1) high performance liquid chromatography (HPLC) with closed-loop recycling and (2) simulated moving bed (SMB) chromatography. HPLC with closed-loop recycling has been known since at least 1959 (R. S. Porter and J. F. Johnson, *Nature*, 183, 391 (1959)). In closed-loop recycling, the chromatographic profile, after eluting from the column and passing through the detector, is directed to the suction side of the solvent pump. The profile is then sent through the column again, i.e. it is recycled. This recycling increases the number of theoretical plates available for the separation, because in essence closed-loop recycling simulates the use of a longer column. Thus, resolution is increased after each cycle. Since mixing occurs in the pump, some of the separation that occurred in the column, is destroyed. Therefore, closed-loop recycling is feasible only when the resolution gained each time the profile passes through the column is greater than the loss in resolution due to mixing each time the profile passes through the pump. In practice this means that the volume of the column must be much larger than the volume of the pump. During any cycle in which sufficient resolution has been attained, fractions are collected or shaved from the leading and trailing edges of the chromatographic profile using collection valves or a stand-alone fraction collector. A review article, discussing the use of closed-loop recycling in the separation of enantiomers, has been recently been published (J. Dingenen and J. N. Kinkel, *J. Chromatography A*, 666, 627 (1994)).

SMB chromatography was invented in the early 1960's by workers at UOP (D. B. Broughton, R. W. Neuzil, J. M. Pharis, C. S. Brearley, *Chem. Eng. Progress*, 66(9), 70 (1970)). SMB chromatography is a continuous process, in which feed is continuously injected into the interior of the circulating SMB profile; two product streams (extract and raffinate) are continuously collected; and fresh mobile phase is also added continuously. The entire profile travels around the system. For example in an SMB system having a 16 column array, at a particular time the feed is injected between columns 7 and 8; the mobile phase is injected between columns 16 and 1; the raffinate is collected between columns 11 and 12; and the extract is collected between columns 3 and 4. When the profile moves a sufficient distance through the system, all the injection and collection points will be switched simultaneously one column length. For example the feed point will be switched to between columns 9 and 10; the mobile phase point, to between columns 1 and 2; the raffinate point to between columns 12 and 13; and the extract point, to between columns 4 and 5. The switching occurs periodically at the appropriate times. At steady state a mass balance is maintained in which the quantity of each component injected is equal to the quantity of each component collected. At steady state the chromatographic profile remains constant in shape and composition. A further characteristic of SMB chromatography is that there are four flow rates across the profile. It is also important to stress that SMB chromatography is truly continuous: the mobile phase and feed pumps never stop pumping material into the system; the extract and raffinate lines never stop delivering collected purified material.

In preparative HPLC with closed-loop recycling, subsequent injections are made only after all components of the sample have been collected or sent to waste. Thus, in ordinary preprative HPLC with closed-loop recyling (or any other type of batch-mode chromatography), fresh sample is never injected into the inerior of the chromatographic profile.

With simulated moving bed (SMB) chromatography, fresh sample is continuously injected into the interior of the circulating chromatographic profile, and two product streams are continuously collected from either end of the profile. SMB is thus a binary separation process because only two fractions are collected. Injecting into the interior of the profile makes the separation inherently a binary separation process.

SUMMARY OF THE INVENTION

An object of the invention is to provide economical and efficient preparative HPLC processes. Another object is to provide apparatuses for such processes.

Still another object is to provide that no loss of the circulating profile occurs during the injection onto the maintained circulating profile.

Upon further study, of the specification and appended claims, further objects and advantages of this invention will become apparent to those skilled in the art.

To achieve those objects, one aspect of the invention is to provide a preparative chromatographic closed loop steady state cyclical process utilizing a single column comprising, at steady state conducting the following steps:

a. establishing and maintaining a circulating chromatographic profile through said column and through one solvent pump;

b. discontinuously and at each cycle injecting a sample comprising at least two components, into the interior of said maintained circulating profile of said single column, said injecting being conducted by an injection loop controlled in an inject position by an injection valve so as to inject the sample in the loop into the interior of said circulating profile, said injection valve remaining in the inject position from the time of injection until all of the profile has eluted from the column, and then adjusting the injection valve to a load position to load the injection loop when all the profile is on the column, and c. collecting, discontinuously and periodically, at least two enriched fractions from said circulating profile.

According to another aspect of the invention, all events in a cycle subsequent to the initiation of collection of the first fraction are referenced with respect to time to the initiation of collection of the first fraction, and the mobile phase pump can be switched off during collection of the last fraction near the end of a cycle. This aspect of the invention results in a very reproducible average circulation time for the chromatographic profile and thus in a process that is very reproducible from cycle to cycle. Furthermore, this aspect of the invention allows an automatic compensation to variances in circulation time of the chromatographic profile due to minor variances in factors such as temperature, mobile phase strength, pumping speed, etc.

To perform the process of the invention, features of the apparatus comprise: a solvent pump, an injection pump, an injection valve and injection loop, collection valves, a recycle valve, and a chromatographic column packed with suitable stationary phase. Any type of preparative chromatographic column can be used.

In a preferred modification of the invention, a detector is employed, although a detector is not essential for the performance of the invention. By virtue of the preferred use of the detector, the entire process becomes visual and intuitive, greatly facilitating methods development. More importantly, the detector allows the use of software in the initiation of all collection and control events such as the collection of fractions, the injection of fresh sample, pump control, etc. By measuring parameters such as the ascending or descending slope, characteristic absorbance, functions of absorbances, characteristic optical activity, refractive index, pH, etc., such software determines the correct point on the chromatographic profile to initiate a given event.

The software also permits collection and control events to be timed events. It is preferred that some, if not all, control events including, but not limited to, valve switching, toggling on and off of pumps, and adjusting pump flow rates, are initiated by the software solely on the basis of time. Conversely, where no detector is used, it is preferred that the progress and success of the separation is determined by periodic and/or on-line sampling of fractions followed by analysis of the fractions by analytical instruments not associated with the preparative chromatographic process.

For best results the process of the current invention should be automated through use of conventional computer and control software. Although not recommended, it is feasible for the process to be operated manually.

The process can be used to perform any type of chromatographic separation including, but not limited to, normal phase chromatographic separations, reverse phase chromatographic separations, chiral chromatographic separations, ion exchange chromatographic separations, affinity chromatographic separations, and size exclusion chromatographic separations. The process of the current invention can be carried out at any scale, both much larger and smaller that those of the examples that will be presented later.

COMPARISON TO PRIOR ART SYSTEMS

In the current invention, sample is injected periodically and discontinuously into the interior of the circulating chromatographic profile. It is similar to SMB in that sample is injected into the interior of the profile. It is different from SMB in that the process is not continuous. As with SMB, fractions are collected on either end of the profile. It is therefore essentially a binary separation technique. Although more than two fractions can easily be collected, the process is still binary because the fractions are taken only from the front and rear portions of the profile.

The advantages, relative to conventional and closed-loop recycling chromatography, of injecting into the interior of the profile are the following:

Only a small amount of resolution of the peaks is necessary. Thus relatively inexpensive stationary phases can be used to pack the columns.

Because high resolution is not needed, high flow rates can be used. This significantly increases productivity.

Because high resolution is not needed, strong mobile phases can be used. This significantly increases productivity.

Because one injects into the interior of the profile, injections occur much more often. This significantly increases productivity.

The prior art contains three patents that are relevant: U.S. Pat. Nos. 4,267,054, 4,379,751, and 4,970,002. Although the processes in these patents feature closed-loop recycling and intra-profile injection of sample, they require two columns or a very complicated column that in essence is a two-column system. The current invention utilizes only a single preparative HPLC column.

Also in the prior art is an article by M. Bailly and D. Tondeur (*Chem. Eng. Sci.* 37(8), 1199–1212, 1982) in which a recycling chromatographic process is described that involves thoroughly mixing the entire recycled chromatographic profile with fresh sample and reinjecting. In the process described by Bailly and Tondeur, the resolution that developed in the chromatographic profile as a result of its passage through the column is destroyed by mixing the entire profile with fresh sample prior to reinjection. The current invention utilizes a precise injection of fresh sample at a precise location in the maintained circulating chromatographic profile. No significant mixing occurs between the fresh sample and the circulating chromatographic profile prior to or during the injection process. The current invention is therefore a superior process in that the resolution developed in the chromatographic profile, as a result of its passage through the column is not destroyed by mixing with sample prior to injection.

BRIEF DESCRIPTION OF THE DRAWINGS

For a better understanding of the present invention, a detailed description of the method of chromatographic separation of fluid mixtures into fractions and Examples illustrating the chromatograph embodiments are given with reference to the accompanying drawings, wherein.

DETAILED DESCRIPTION OF THE DRAWINGS

Figure 1:
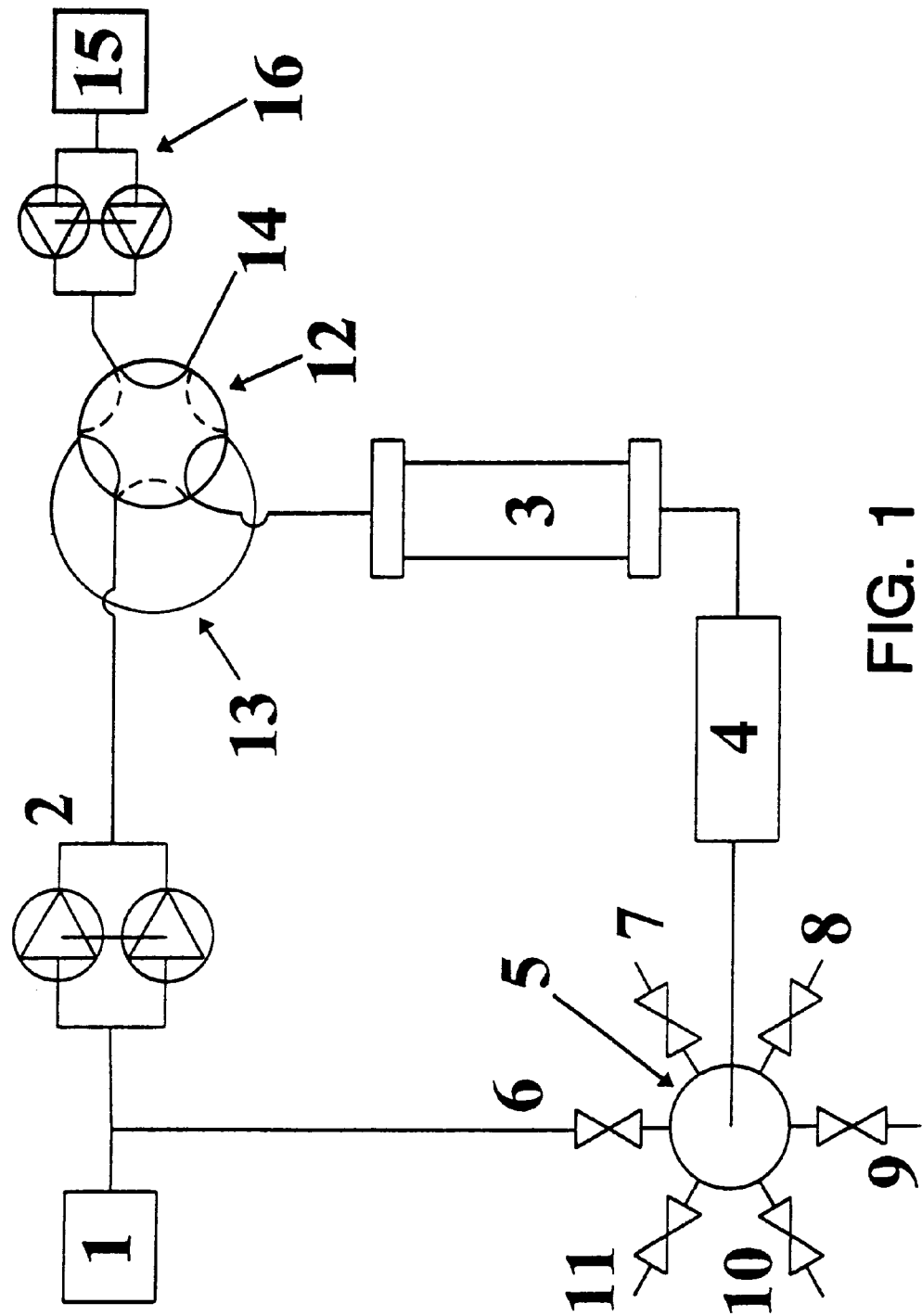
FIG. 1 is a schematic flow sheet of a preferred embodiment of the invention.
Figure 2:
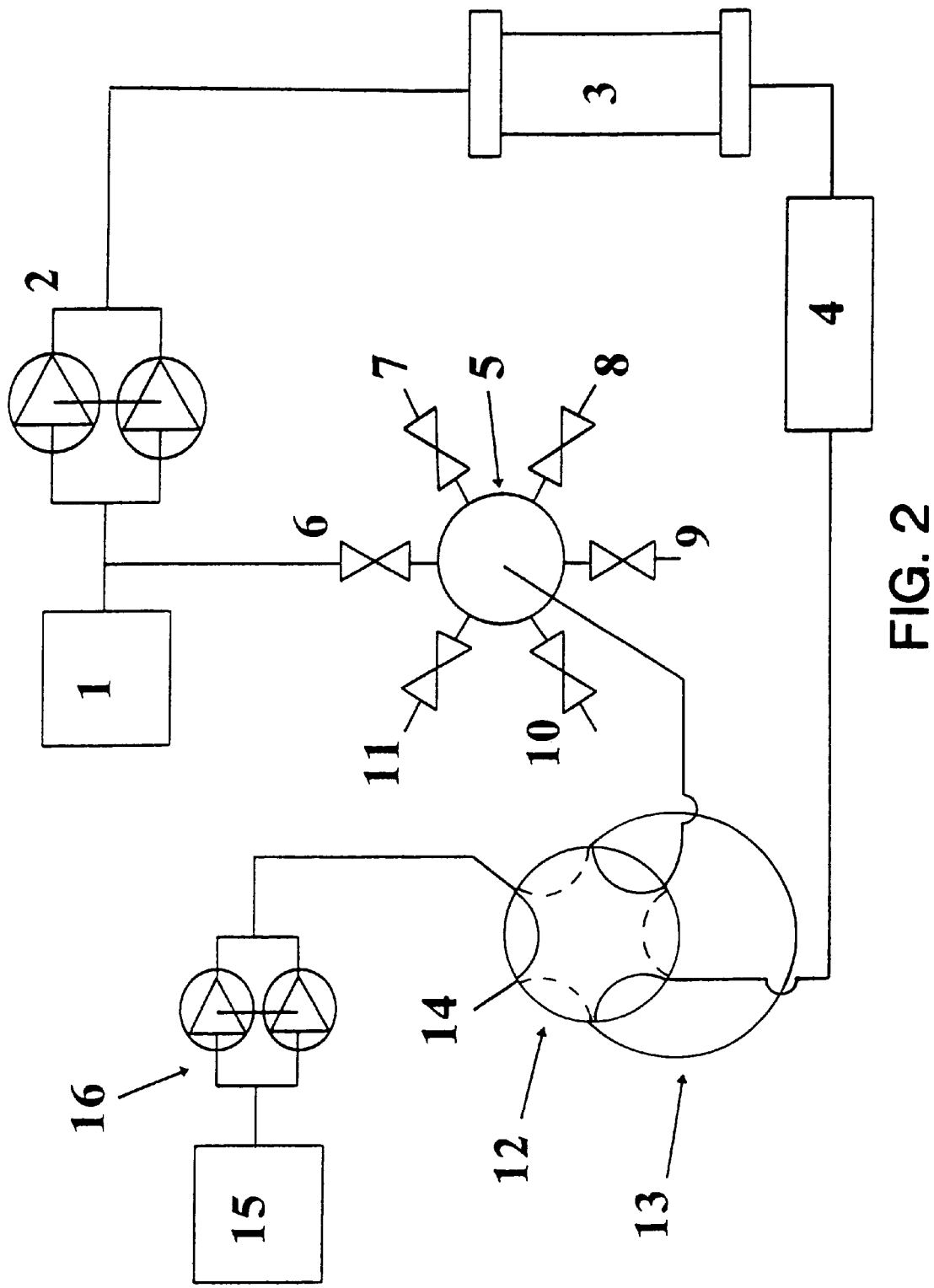
FIG. 2 is a schematic flow sheet of another preferred embodiment of the invention, differing from FIG. 1 in placement of the injection valve and injection loop.

Referring to FIGS. 1 and 2, the components of the invention are identified by the following numbers:

1 is the solvent reservoir. The solvent pump 2 draws fresh mobile phase from the solvent reservoir 1 as needed whenever collection valves 7–10 or waste valve 11 are open.

2 is the solvent pump. The pumping rate of the solvent pump 2 is typically controlled by the control software but may be adjusted manually.

3 is the chromatographic column. Any type of column typically used in preparative HPLC can be used.

4 is the detector. The detector can be a UV-visible, refractive index, conductivity, or any type of detector typically used in preparative HPLC. For best results, a full-flow sample cell should be used.

5 is the valve distribution manifold though which effluent from the column 3 and detector 4 is directed to either of valves 6–11, only one of which can be opened at any one time.

6 is the recycle valve. When this valve is open, the effluent from the column 3 and detector 4 is directed to the suction side of the solvent pump 2. The recycle valve 6 is opened when all or part of the chromatographic profile is to be recycled through the column 3. The recycle valve 6 is typically controlled by the control software.

7, 8, 9, and 10 are fraction collection valves. One of these valves is opened when it is desired to collect a fraction. These valves are typically controlled by the control software.

11 is the waste valve. This valve is opened when it is desired to send the effluent from the column 3 and detector 4 to waste. This valve is typically controlled by the control software.

Components 12–16 make up the sample injection system.

12 is the 6-port injection valve.

13 is the injection loop.

14 is the waste port of the injection valve 12.

15 is the sample reservoir.

16 is the sample injection pump.

OPERATION OF THE INVENTION

The following is a description of the operation of the preferred embodiment shown in FIG. 1:

At the beginning of a run, the injection loop 13 is filled with sample. To accomplish this, the injection valve 12 is placed in the load position indicated by the dotted-line flow path, and the injection pump 16 is switched on. Sample is thus drawn from the sample reservoir 15 and pumped into the injection loop 13. When the injection loop 13 is filled, the injection pump 16 is switched off Any excess sample goes to waste through waste port 14. During this initial filling of the injection loop 13, the solvent pump 2 draws mobile phase from the mobile phase reservoir 1. The effluent from the column 3 and detector 4 follows the dotted-line flow path through the injection valve 12 and goes to waste through valve 11.

The initial injection of sample is accomplished as follows. Simultaneously, the injection valve 12 is placed in the inject position indicated by the solid-line flow path, the recycle valve 6 is opened, and the waste valve 11 is closed. The solvent pump 2 causes the mobile phase to be circulated in a clockwise direction around the system as depicted in FIG. 1. The sample in the injection loop 13 is therefore conducted through the recycle valve 6, through the solvent pump 2, and onto the column 3. When all of the sample originally in the injection loop 13 has been pumped onto the column 3, the initial injection is complete.

The repetitive phase of the process now begins. The following sequence of events occurs each cycle:

Event 0-1

When all of the chromatographic profile is on the column 3, i.e. after the entire profile has been conducted onto the column 3 and before any of the profile elutes from the column 3, the injection valve 12 is switched to the load position indicated by the dotted-line flow path; the waste valve 11 is opened; and any of the other valves 6–10 that may have been opened is closed. The effluent from the column 3 and detector 4 follows the dotted-line flow path through the injection valve 12 and goes to waste through valve 11. This waste collection step prevents any circulating impurities from contaminating future fractions. During this event, the solvent pump 2 is switched on and draws fresh mobile phase from solvent reservoir 1 to make up the mobile phase lost through the waste valve 11.

Event 0-2

At the appropriate time the injection loop 13 is filled with sample as described above by switching on the sample injection pump 16 for the required amount of time. During this event the effluent from the column 3 and detector 4 goes to waste through the waste valve 11. This waste collection step prevents any circulating impurities from contaminating future fractions. During this event, fresh mobile phase is drawn from solvent reservoir 1 by the solvent pump 2 to make up the mobile phase lost through the waste valve 11.

Event 0-3

As the chromatographic profile elutes from the column 3, the detector 4 detects the leading edge of the profile. One of the collection valves 7–10 is opened to collect a fraction from the leading edge of the profile, defined as Fraction 1. By way of example and to make a clear description of the process, valve 7 will be designated as the collection valve for Fraction 1. Simultaneously with the opening of valve 7 to collect Fraction 1, the waste valve 11 is closed. During collection of Fraction 1, fresh mobile phase is drawn from solvent reservoir 1 by the solvent pump 2 to make up the mobile phase lost during collection of Fraction 1.

Event 0-4

At the appropriate time, valve 7 closes and the recycle valve 6 opens. This stops the collection of Fraction 1 and directs the rest of the chromatographic profile through the solvent pump 2 and onto the column 3. No mobile phase is drawn from the solvent reservoir 1 by solvent pump 2 when the recycle valve 6 is opened, because no mobile phase is lost through any of the closed valves 7–11.

Event 0-5

At the appropriate time as the central part of the chromatographic profile elutes from the column 3, the injection valve 12 is switched to the inject position indicated by the solid-line flow path. Effluent from the column 3 and detector 4 is diverted through the injection loop 13. Thus, fresh sample is injected into the interior of the chromatographic profile at the appropriate point in the profile. The profile proceeds through the recycle valve 6, through the solvent pump 2, and onto the column 3.

Event 0-6

As the chromatographic profile continues to elute from the column 3 and detector 4, and at the appropriate time, one of the collection valves 7–10 is opened to collect a fraction from the trailing edge of the profile, defined as Fraction 2. By way of example and to make a clear description of the process, valve 9 will be designated as the collection valve for Fraction 2. During collection of Fraction 2, fresh mobile phase is drawn from solvent reservoir 1 by the solvent pump 2 to make up the mobile phase lost during collection of Fraction 2. The chromatographic profile that was recycled onto the column 3 in Events 1-4 and 1-5 continues to travel down the column under the influence of the solvent pump 2.

Event 0-7

At the appropriate time, valve 9 closes and another of the valves 7–11 opens. By way of example and to make a clear description of the process, valve 10 will be designated as the collection valve for this event. This event occurs after most of the trailing edge has been collected as Fraction 2; i.e. this event occurs in the "tail" of the profile when the profile has returned almost to baseline as measured by the detector 4. Thus, this event can be thought of as the collection of a very dilute fraction or of a waste fraction, in either case defined as Fraction 3. This collection event continues until all of the "tail" of the profile is collected. The chromatographic profile that was recycled onto the column 3 in Events 1-4 and 1-5 continues to travel down the column under the influence of the solvent pump 2.

Event 0-8

(Optional). Event 1-8 provides, in a novel way, extremely reproducible cycles on a time basis. The solvent pump 2 is switched off sometime after the initiation of Event 1-7. Event 1-8 is used only if Events 1-4 through 1-7 are referenced with respect to time to Event 1-3. In such a case, Event 4 will occur a predetermined amount of time after the initiation of Event 1-3, Event 5 will occur a predetermined amount of time after the initiation of Event 1-3, etc. Event 1-8 is also referenced with respect to time to Event 1-3; ie., Event 1-8 will occur a predetermined amount of time after the initiation of Event 1-3. After the initiation of Event 1-8, the solvent pump 2 will remain switched off until the end of the cycle. If Event 1-8 were not used, and if a cycle time were chosen that was slightly longer than the true circulation time of the chromatographic profile, the profile would drift to earlier and earlier times each cycle, and eventually the leading edge of the profile would occur before the start of the cycle. Conversely, if the a cycle time were chosen that was slightly shorter than the true circulation time of the chromatographic profile, the profile would drift to later and later times each cycle, and eventually the trailing edge of the profile would carry over into the next cycle. To use Event 1-8, a cycle time is chosen that is slightly longer than the true circulation time of the profile. The profile will then tend to drift to earlier times. However, this will cause the solvent pump 2 to be off for a longer time, thus decreasing the average velocity of the circulating profile. If the profile slows down too much, the profile will tend to drift to longer times. This will cause the solvent pump 2 to be off for a shorter time, thus increasing the average velocity of the circulating profile. Thus the circulation time of the profile is forced to oscillate slightly about the chosen cycle time. This results in a very reproducible average circulation time for the chromatographic profile and thus in a process that is very reproducible from cycle to cycle. This technique allows an automatic compensation for variances in average circulation time of the chromatographic profile due to minor variances in factors such as temperature, mobile phase strength, pumping speed, etc. If Event 1-8 is not used, the absolute times of each control and collection event is entered into the control software.

The cycle ends either with the end of Event 1-7 or 1-8 and the sequence of events begins again with Event 1-1. The process is repeated multiple times. Eventually a mass balance develops; i.e., the amount of each component collected in the fractions is equal to the amount of each component injected. The chromatogram then has the appearance of a steady state process; i.e., the shape of the chromatographic curve as measured by the detector is virtually identical for each cycle. This state could be accurately described as a periodic steady state, in that the profile expands and contracts in size as it travels around the circuit, depending on whether sample is being injected, fractions are being collected, or whether the profile is simply traveling down the column and undergoing the separation process. For reasons of brevity, henceforth this state will be referred to as a steady state. Once the process has reached steady state, the process can be repeated as many times as necessary until the desired amount of sample has been separated.

The following is a description of the operation of the preferred embodiment shown in FIG. 2:

At the beginning of a run, the injection loop 13 is filled with sample. To accomplish this, the injection valve 12 is placed in the load position indicated by the dotted-line flow path, and the injection pump 16 is switched on. Sample is thus drawn from the sample reservoir 15 and pumped into the injection loop 13. When the injection loop 13 is filled, the injection pump 16 is switched off. Any excess sample goes to waste through waste port 14. During this initial filling of the injection loop 13, the solvent pump 2 draws mobile phase from the mobile phase reservoir 1 and pumps it through the dotted-line flow path of the injection valve 12 and onto the column 3. The effluent from the column 3 and detector 4 goes to waste through valve 11.

The initial injection of sample is accomplished as follows. The injection valve 12 is placed in the inject position indicated by the solid-line flow path. The solvent pump 2 pumps mobile phase through the injection loop 13 and onto the column 3. The sample in the injection loop 13 is therefore conducted onto the column 3. When all of the sample originally in the injection loop 13 has been pumped onto the column 3, the initial injection is complete.

The repetitive phase of the process now begins. The following sequence of events occurs each cycle:

Event 2-1

When all of the chromatographic profile is on the column 3, i.e. after the entire profile has been conducted onto the column 3 and before any of the profile elutes from the column 3, the injection valve 12 is switched to the load position indicated by the dotted-line flow path; the waste valve 11 is opened; and any of the other valves 6–10 that may have been opened is closed. Mobile phase is pumped from the solvent reservoir 1 by the solvent pump 2 through the dotted-line flow path of the injection valve 12 and onto the column 3. The effluent from the column 3 and detector 4 goes to waste through the waste valve 11. This waste collection step prevents any circulating impurities from contaminating future fractions.

Event 2-2

At the appropriate time the injection loop 13 is filled with sample as described above by switching on the sample injection pump 16 for the required amount of time. During this event the effluent from the column 3 and detector 4 goes to waste through the waste valve 11. This waste collection step prevents any circulating impurities from contaminating future fractions. During this event, fresh mobile phase is drawn from solvent reservoir 1 by the solvent pump 2 to make up the mobile phase lost through the waste valve 11.

Event 2-3

As the chromatographic profile elutes from the column 3, the detector 4 detects the leading edge of the profile. One of the collection valves 7–10 is opened to collect a fraction from the leading edge of the profile, defined as Fraction 1. By way of example and to make a clear description of the process, valve 7 will be designated as the collection valve for Fraction 1.

Simultaneously with the opening of valve 7 to collect Fraction 1, the waste valve 11 is closed. During collection of Fraction 1, fresh mobile phase is drawn from solvent reservoir 1 by the solvent pump 2 to make up the mobile phase lost during collection of Fraction 1.

Event 2-4

At the appropriate time, valve 7 closes and the recycle valve 6 opens. This stops the collection of Fraction 1 and directs the rest of the chromatographic profile through the solvent pump 2, through the dotted-line flow path of the injection valve 12 and onto the column 3. No mobile phase is drawn from the solvent reservoir 1 by solvent pump 2 when the recycle valve 6 is opened, because no mobile phase is lost through any of the closed valves 7–11.

Event 2-5

At the appropriate time as the central part of the chromatographic profile elutes from the column 3 and is conducted through the recycle valve 6 and through the solvent pump 2, the injection valve 12 is switched to the inject position indicated by the solid-line flow path. Effluent from the solvent pump 2 is diverted through the injection loop 13. Thus, fresh sample is injected into the interior of the chromatographic profile at the appropriate point in the profile. The profile proceeds through the injection loop 13 and onto the column 3.

Event 2-6

As the chromatographic profile continues to elute from the column 3 and detector 4, and at the appropriate time, one of the collection valves 7–10 is opened to collect a fraction from the trailing edge of the profile, defined as Fraction 2. By way of example and to make a clear description of the process, valve 9 will be designated as the collection valve for Fraction 2. During collection of Fraction 2, fresh mobile phase is drawn from solvent reservoir 1 by the solvent pump 2 to make up the mobile phase lost during collection of Fraction 2. The chromatographic profile that was recycled onto the column 3 in Events 2-4 and 2-5 continues to travel down the column under the influence of the solvent pump 2.

Event 2-7

At the appropriate time, valve 9 closes and another of the valves 7–11 opens. By way of example and to make a clear description of the process, valve 10 will be designated as the collection valve for this event. This event occurs after most of the trailing edge has been collected as Fraction 2; i.e. this event occurs in the "tail" of the profile when the profile has returned almost to baseline as measured by the detector 4. Thus, this event can be thought of as the collection of a very dilute fraction or of a waste fraction, in either case defined as Fraction 3. This collection event continues until all of the "tail" of the profile is collected. The chromatographic profile that was recycled onto the column 3 in Events 2-4 and 2-5 continues to travel down the column under the influence of the solvent pump 2.

Event 2-8

(Optional). As explained previously for Event 1-8, Event 2-8 provides, in a novel way, extremely reproducible cycles on a time basis. The solvent pump 2 is switched off sometime after the initiation of Event 2-7. Event 2-8 is used only if Events 2-4 through 2-7 are referenced with respect to time to Event 2-3. In such a case, Event 2-4 will occur a predetermined amount of time after the initiation of Event 2-3, Event 2-5 will occur a predetermined amount of time after the initiation of Event 2-3, etc. Event 2-8 is also referenced with respect to time to Event 2-3; i.e., Event 2-8 will occur a predetermined amount of time after the initiation of Event 2-3. After the initiation of Event 2-8, the solvent pump 2 will remain switched off until the end of the cycle. The mechanism and benefits described above for Event 1-8 also apply to Event 2-8.

The cycle ends either with the end of Event 2-7 or 2-8 and the sequence of events begins again with Event 2-1. The process is repeated multiple times. Eventually a mass balance develops; i.e., the amount of each component collected in the fractions is equal to the amount of each component injected. The chromatogram then has the appearance of a steady state process; ie., the shape of the chromatographic curve as measured by the detector is virtually identical for each cycle. As indicated above, this state could be accurately described as a periodic steady state, in that the profile expands and contracts in size as it travels around the circuit, depending on whether sample is being injected, fractions are being collected, or whether the profile is simply traveling down the column and undergoing the separation process, and is hereinafter referred to as a steady state. Once the process has reached steady state, the process can be repeated as many times as necessary until the desired amount of sample has been separated.

In the current invention all switching occurs sequentially, not simultaneously as in SMB. The process of the current invention is therefore not continuous but rather discontinuous and repetitive. At steady state, the time between the same event in succeeding cycles will be constant and is called the cycle time. For example, assume the cycle time is 6 minutes. In a certain cycle, say cycle 30, the injection valve 12 is switched to the load position indicated by the dotted-line flow path in FIG. 1. Six minutes later, the injection valve 12 is again switched to the load position; six minutes later, it will again switch to the load position; etc. Likewise, at a later time in cycle 30, collection valve 7 will open to collect Fraction 1; six minutes later collection valve 7 will again open to collect Fraction 1; etc. This happens for all the events in each cycle. They all occur again and again the interval between the same occurrence equaling the cycle time.

The current invention is a repetitive process that can run for hours or days on end. It is, therefore, preferable that it be automated via computer control. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, temperatures are set forth uncorrected in degrees Celsius and unless otherwise indicated, all parts and percentages are by weight.

TurboPrep® control software, proprietary software of EM Industries, Inc., was used in all runs discussed in the examples that follow. The software ran on a 486 computer from Dell Computer Corporation. The interface between computer and equipment was from Opto 22.

In the examples that follow the solvent pump 2 was an ST 140 preparative HPLC pump from EM Industries, Inc., Hawthorne, N.Y. The flow rate of the solvent pump was set with the control software. The injection pump 16 was an Eldex model B-100-S4 metering pump. The flow rate for this pump was set manually with a micrometer. The Eldex pump was switched on and off via the control software.

The injection valve 12 and its air-powered actuator were obtained from Rheodyne. The recycle valve 6, the waste valve 11 and the collection valves 7–10 were obtained from Mace. All valves were air actuated and were controlled via the control software.

The detector 4 was obtained from Knauer. It was a variable wavelength UV HPLC detector equipped with a high pressure flow cell.

The column 3 had the following dimensions: 2.5 cm internal diameter×25 cm long. The column was packed by Modcol (St. Louis, Mo.) with Lichrospher C18, 12 $\mu$m particle size, 100 □ pore diameter. Lichrospher C18 is a silica-based bonded phase from Merck KGaA of Darmstadt, Germany.

The following experimental conditions were used. The mobile phase was methanol:water 90:10 by volume. Both the methanol and the water were HPLC grade and were obtained from EM Science, Gibbstown, N.J. The nominal flow rate for the solvent pump 2 was 20 mL/min.

The mixture undergoing separation was a solution of methyl and propyl p-hydroxybenzoates. The methyl and propyl p-hydroxybenzoates were obtained from Aldrich. The sample solution was made by dissolving 30 mg/mL each of methyl and propyl p-hydroxybenzoate in methanol:water 80:20 by volume. The methyl p-hydroxybenzoate is less retained and eluted first; the propyl p-hydroxybenzoate eluted second.

EXAMPLE 1

This example, a run of 42 cycles, used the preferred embodiment depicted in FIG. 1. The cycle time was set at 6.1 min. The other operating conditions are those given in the previous section. The nominal flow rate of the Eldex injection pump 16 was set at 20 mL/min. Each injection occurred for 0.25 minute giving an injection volume of 5.0 mL. Thus 150 mg each of methyl and propyl p-hydroxybenzoate were injected each time.

Figure 3:
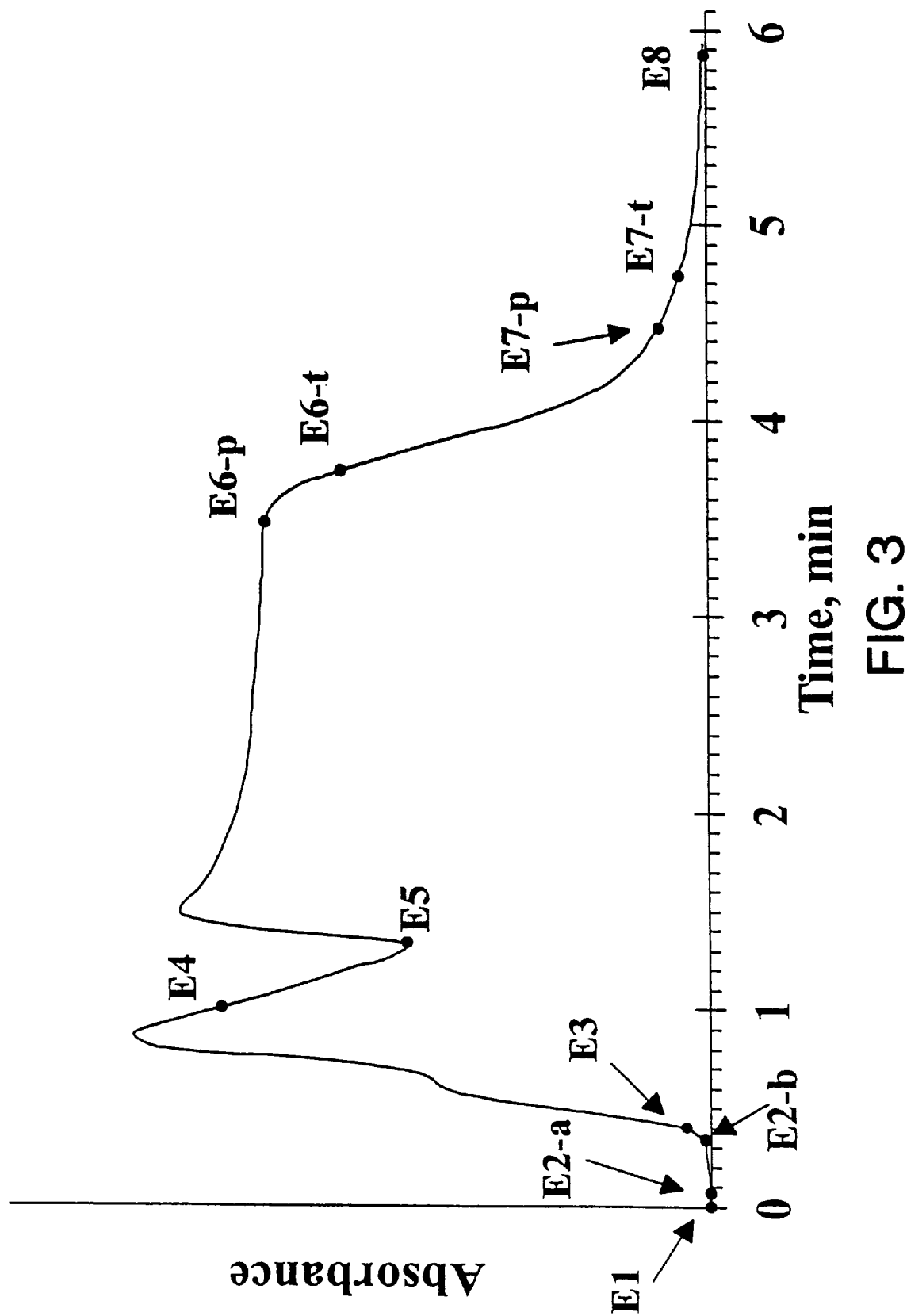
FIG. 3 is the chromatogram of Cycle 41 of Example 1.

Event 1-3, the initiation of collection of Fraction 1, was triggered by the detection of the rising slope of the chromatographic profile. Specifically, valve 7 was opened and valve 11 was closed when a rising slope equal to 20% of the maximum detector signal per second was detected by the software. Events 1-4 through 1-8 were each triggered at set amounts of time after the initiation of Event 1-3. FIG. 3 shows the chromatogram of a typical steady state cycle, in this case Cycle 41. The eight events discussed above are labeled in FIG. 3 as follows:

E1 indicates Event 1-1: The injection valve 12 was placed in load position, indicated by the solid-line flow path in FIG. 1. The waste valve 11 was opened. This event occurred at 0.0 minutes in the cycle.

E2-a indicates the beginning of Event 1-2: The injection pump 16 was switched on to fill the injection loop 13. This event occurred at 0.10 minutes in the cycle.

E2-b indicates the end of Event 1-2: The injection pump 16 was switched off, the injection loop 13 having been filled. This event occurred at 0.35 minutes in the cycle.

E3 indicates Event 1-3: Valve 7 was opened to begin collection of Fraction 1, methyl p-hydroxybenzoate. This event occurred when a rising slope equal to 20% of the maximum detector signal per second was detected by the software. As shown in Table 1, this event occurred at about 27 seconds or about 0.45 minutes in the cycle.

E4 indicates Event 1-4: Valve 7 was closed to stop collection of Fraction 1. The recycle valve 6 was opened to allow the unresolved chromatographic profile to be recycled onto the column 3 via the solvent pump 2. This event occurred 0.60 minutes after initiation of Event 1-3 or about 1.05 minutes in the cycle.

E5 indicates Event 1-5: The injection valve 12 was switched to the inject position, indicated by the solid-line flow path in FIG. 1. The interior of the chromatographic profile was thus diverted to travel through the injection loop 13. This resulted in 5.0 mL of fresh sample, 150 mg of methyl p-hydroxybenzoate and 150 mg of propyl p-hydroxybenzoate, being injected into the interior of the chromatographic profile. This event occurred 0.90 minutes after initiation of Event 1-3 or about 1.35 minutes in the cycle.

E6-p and E6-t indicate Event 1-6: The recycle valve 6 was closed and valve 9 was opened to begin collection of Fraction 2. E6-t indicates the time at which this event occurred, 3.30 minutes after initiation of Event 1-3 or about 3.75 minutes in the cycle. Because the profile traveled through the injection loop 13 before reaching the collection valve 9, the part of the profile that was collected by collection valve 9 was that part that passed through the detector 4 approximately 0.25 minutes earlier (5 mL/[20 mL/min]). E6-p indicates, therefore, the point on the profile at which this event occurred, the part of the profile where the collection of Fraction 2 actually began. E6-p therefore occurred approximately 3.05 minutes after initiation of Event 1-3 or about 3.50 minutes in the cycle. In subsequent chromatograms for this example, the beginning of Event 1-6 will be indicated by E6-p.

E7-p and E7-t indicate Event 1-7: The collection valve 9 was closed and collection valve 10 was opened to begin collection of Fraction 3. E7-t indicates the time at which this event occurred, 4.30 minutes after initiation of Event 1-3 or about 4.75 minutes in the cycle. Because the profile traveled through the injection loop 13 before reaching the collection valve 10, the part of the profile that was collected by collection valve 10 was that part that passed through the detector 4 approximately 0.25 minutes earlier (5 mL/[20 mL/min]). E7-p indicates, therefore, the point on the profile at which this event occurred, the part of the profile where the collection of Fraction 3 actually began. E6-p therefore occurred approximately 4.05 minutes after initiation of Event 1-3 or about 4.50 minutes in the cycle. In subsequent chromatograms for this example, the beginning of Event 1-7 will be indicated by E7-p.

E8 indicates Event 1-8: The solvent pump 2 was shut off until the end of the cycle. This event occurred 5.50 minutes after initiation of Event 1-3 or about 5.95 minutes in the cycle. Thus the solvent pump was shut off approximately 0.15 minutes or 9.0 seconds at the end of each cycle. This result implies that the true cycle time, i.e. the circulation time of the chromatographic profile, is approximately 5.95 minutes under the conditions of temperature, flow rate, and mobile phase composition used for this run. Thus this run could have been duplicated by entering directly into the control software this value of the cycle time (5.95 minutes) and the absolute times for each event as determined above (0.0 minutes for E1, 0.10 minutes for E2-a, 0.35 minutes for E2-b, 0.45 minutes for E3, 1.05 minutes for E4, 1.35 for E5, 3.75 minutes for E6-t, and 4.75 minutes for E7-t). E8 would not have been employed if this direct approach had been used.

Figure 4:
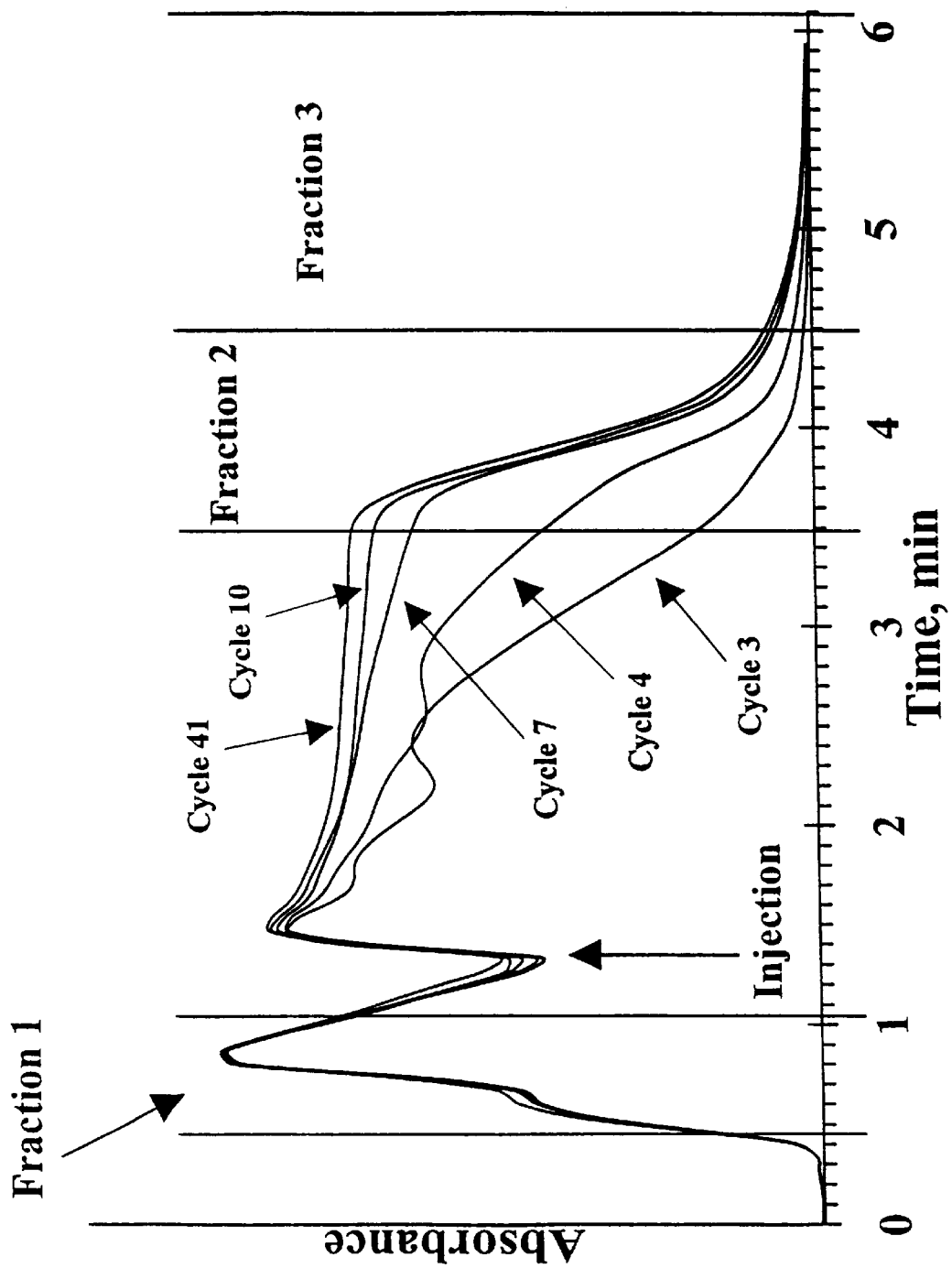
FIG. 4 is the superimposed chromatograms of Cycles 3, 4, 7, 10, and 41 of Example 1.
Figure 5:
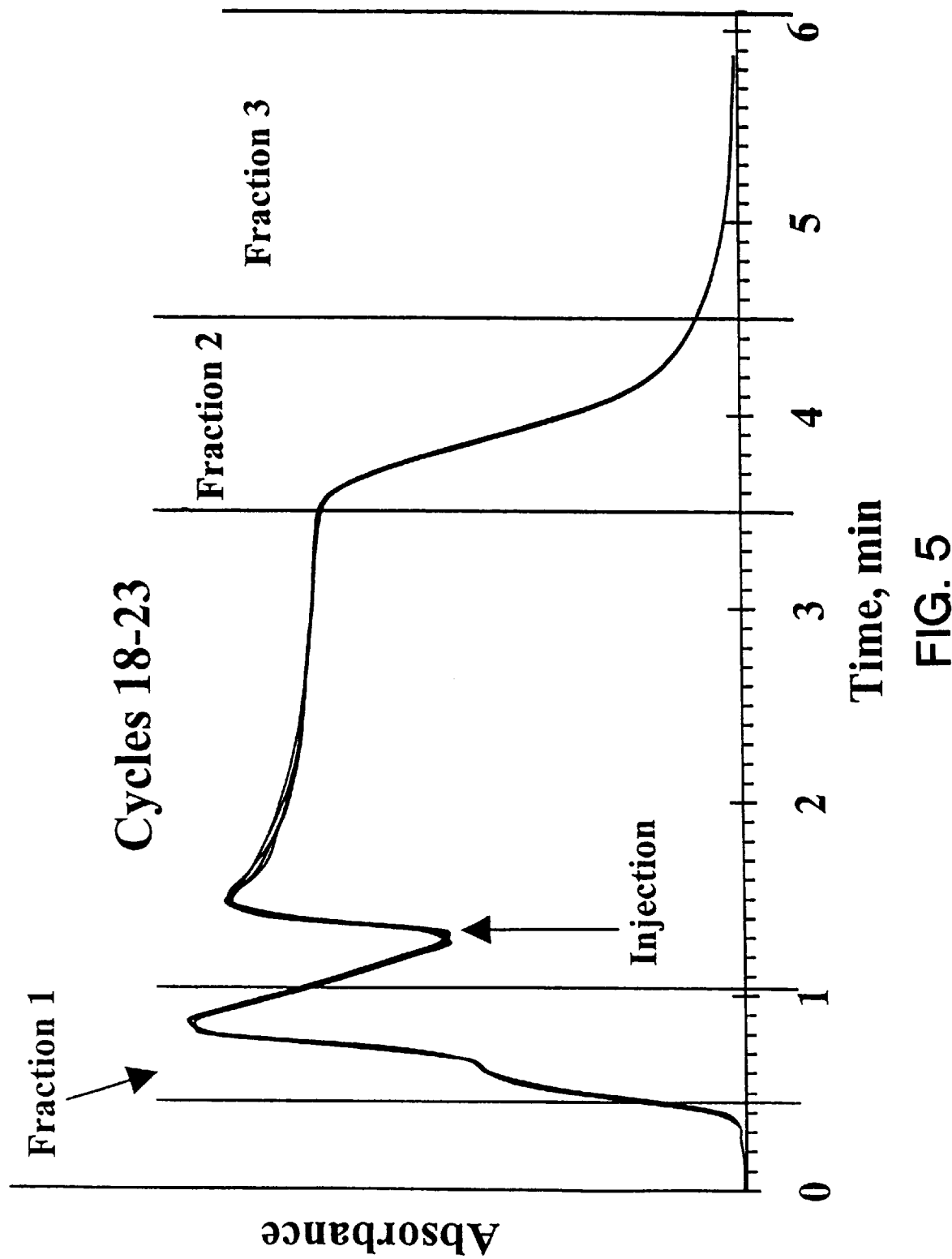
FIG. 5 is the superimposed chromatograms of Cycles 18–23 of Example 1.
Figure 6:
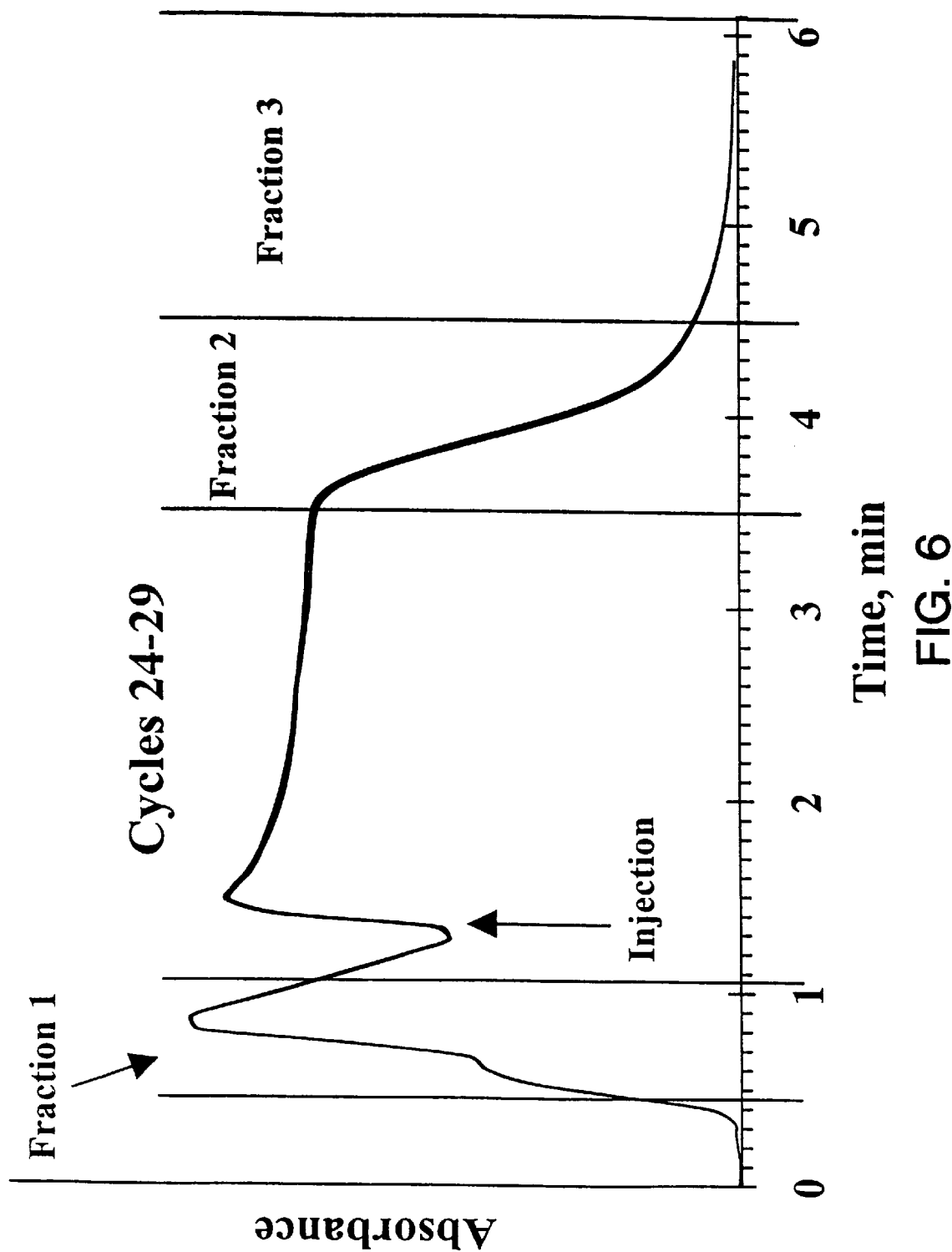
FIG. 6 is the superimposed chromatograms of Cycles 24–29 of Example 1.
Figure 7:
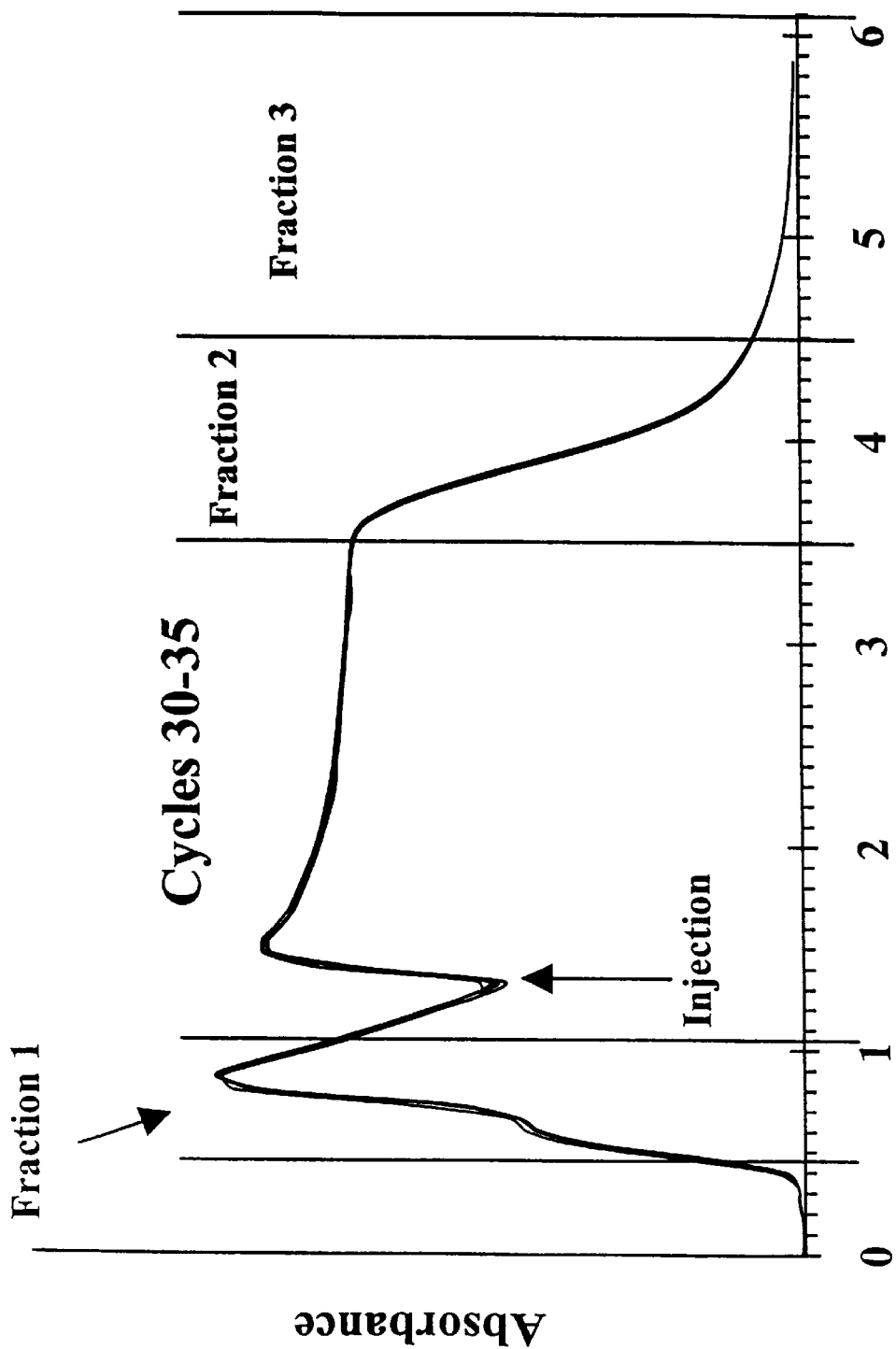
FIG. 7 is the superimposed chromatograms of Cycles 30–35 of Example 1.
Figure 8:
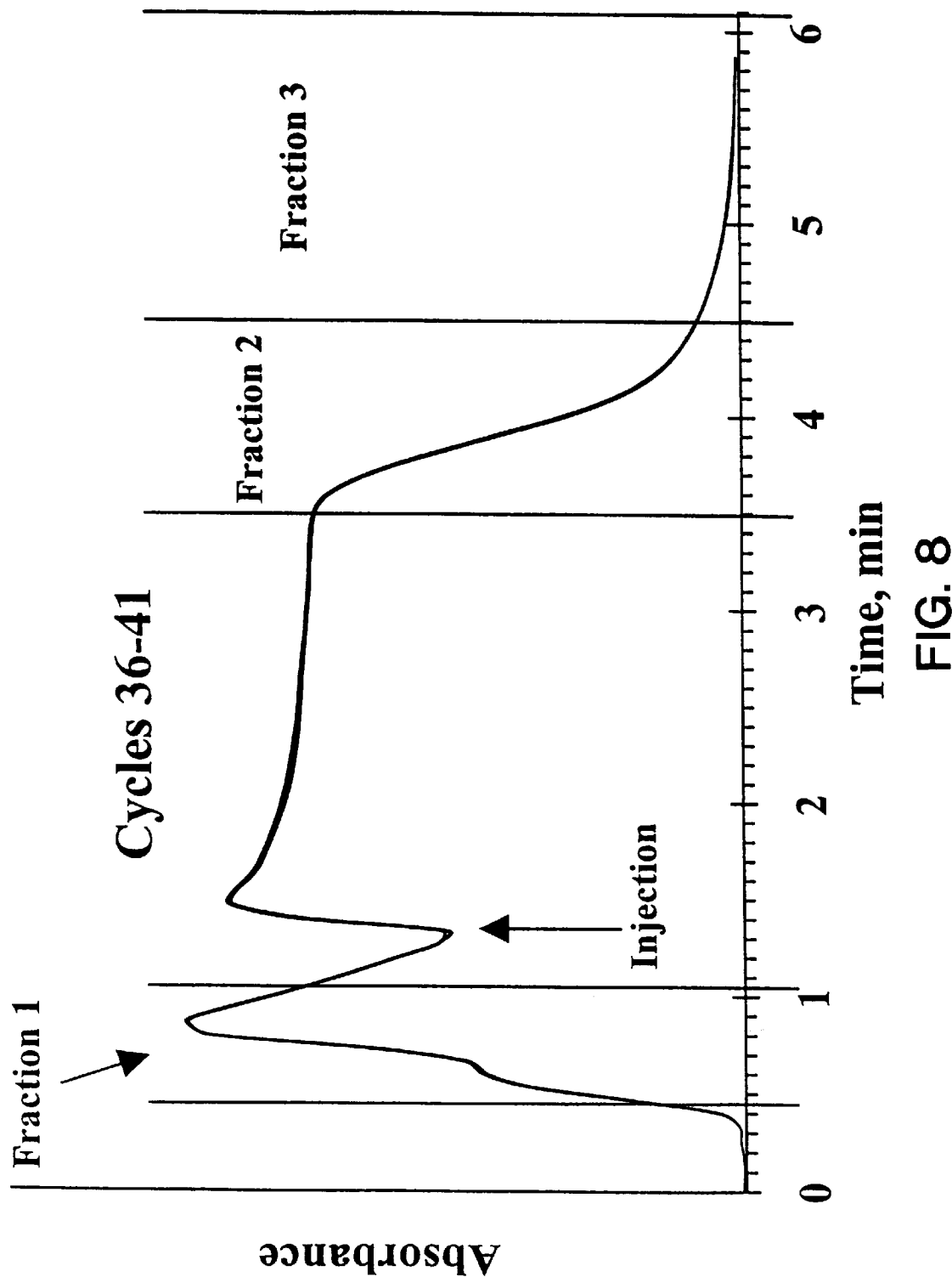
FIG. 8 is the superimposed chromatograms of Cycles 36–41 of Example 1.

FIG. 4 shows the superimposed chromatograms of Cycles 3, 4, 7, 10, and 41. The leading part of the chromatographic profile, through the collection of Fraction 1, reached steady state by Cycle 3. It is estimated, however, that it required about 18 cycles for the rest of the chromatographic profile to reach steady state. That is, the chromatograms for cycles 18–41 are virtually identical. This is illustrated in FIG. 5 (Cycles 18–23), FIG. 6 (Cycles 24–29), FIG. 7 (Cycles 30–35), and FIG. 8 (Cycles 36–41).

Fraction 1 (methyl p-hydroxybenzoate) and Fraction 2 (propyl p-hydroxybenzoate) were analyzed by analytical HPLC using an Hitachi L-6000 pump. The mobile phase was methanol:water 60:40, and the flow rate was 2.0 mL/min. Both the methanol and the water were HPLC grade and were obtained from EM Science. The column, having dimensions 4 mm ID×125 mm, was packed with Lichrospher RP18 (12 μm particle size) and was obtained from Merck KGaA of Darmstadt, Germany. A Rheodyne 6-way valve (model 7000L) equipped with a 20 μL loop was used as the injection valve. The detector was a variable UV wavelength detector from Knauer. The wavelength was set at 285 nm for each analysis.

Figure 9:
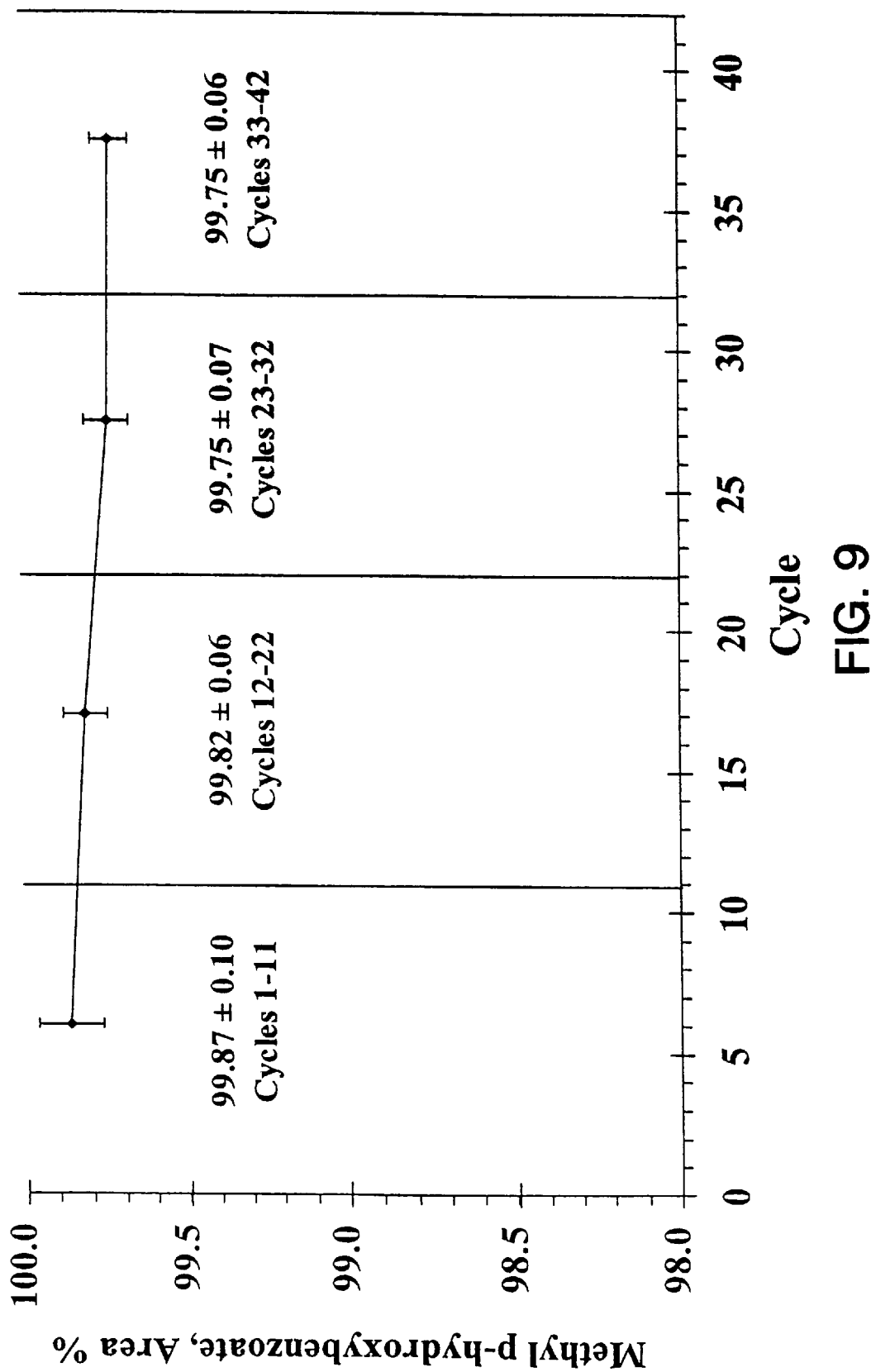
FIG. 9 depicts the analytical results for Fraction 1 of Example 1.

The analytical results for Fraction 1 are shown in FIG. 9. Four bottles were used in turn to collect Fraction 1. The first bottle was used to collect Fraction 1 from Cycles 1–11; the second bottle, Cycles 12–22; the third bottle, Cycles 23–32; and the fourth bottle, Cycles 33–42. The purity of Fraction 1, expressed as area percent, was very high, being 99.8% within experimental error for all cycles. Each purity in FIG. 9 is an average of at least three measurements, and each uncertainty is expressed in the 95% confidence interval.

Figure 10:
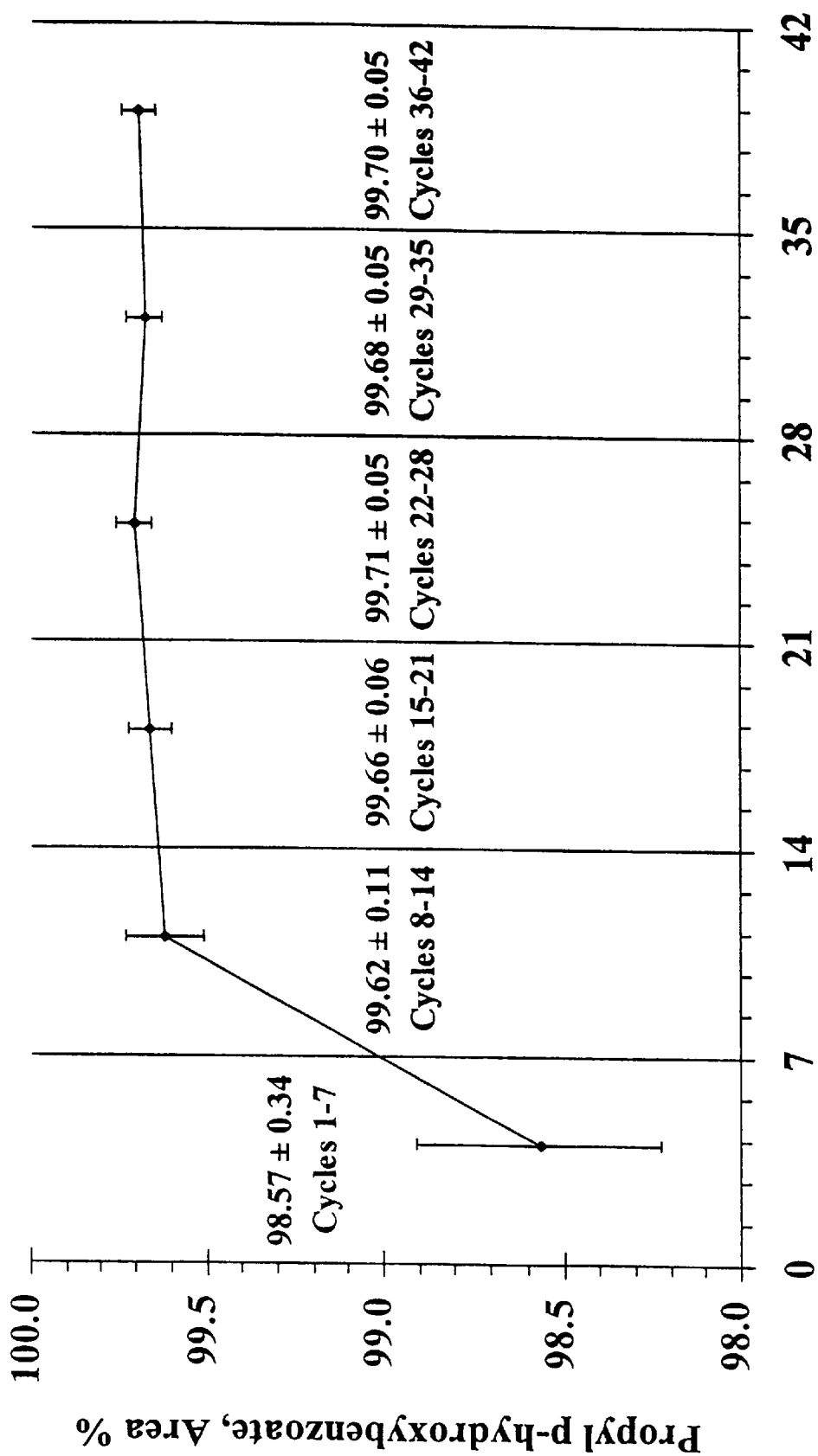
FIG. 10 depicts the analytical results for Fraction 2 of Example 1.

The analytical results for Fraction 2 are shown in FIG. 10. Six bottles were used in turn to collect Fraction 2. The first bottle was used to collect Fraction 2 from Cycles 1–7; the second bottle, Cycles 8–14; the third bottle, Cycles 15–21; the fourth bottle, Cycles 22–28; the fifth bottle, from Cycles 29–35; and the sixth bottle, from Cycles 36–42. The purity of Fraction 2, expressed as area percent, was about 98.6% for Cycles 1–7. The purity of Fraction 2 from all subsequent cycles (Cycles 8–42) was greater than 99.6 area % within experimental error. Thus the steady state purity (Cycles 18–42) of Fraction 2 is very high, greater than 99.6 area % within experimental error. Each purity in FIG. 10 is an average of at least three measurements, and each uncertainty is expressed in the 95% confidence interval.

Table 1 shows the times for each cycle at which Event 1-3, the initiation of collection of Fraction 1, occurred. These times are a measure of the reproducibility of the cycles on a time basis at steady state. As shown, the reproducibility of Event 1-3 is very good. Since all events subsequent to Event 1-3 occurred at set amounts of time after Event 1-3, all event times showed excellent reproducibility from cycle to cycle.

TABLE 1

Time of Initiation of Event 1–3 for Each Cycle

| Cycle | Time, sec | Cycle | Time, sec | Cycle | Time, sec | Cycle | Time, sec |
|---|---|---|---|---|---|---|---|
| 3 | 27 | 13 | 27 | 23 | 27 | 33 | 28 |
| 4 | 27 | 14 | 27 | 24 | 27 | 34 | 23 |
| 5 | 27 | 15 | 27 | 25 | 27 | 35 | 27 |
| 6 | 27 | 16 | 27 | 26 | 27 | 36 | 27 |
| 7 | 27 | 17 | 27 | 27 | 27 | 37 | 27 |
| 8 | 27 | 18 | 27 | 28 | 27 | 38 | 27 |
| 9 | 27 | 19 | 27 | 29 | 27 | 39 | 27 |
| 10 | 27 | 20 | 28 | 30 | 28 | 40 | 27 |
| 11 | 26 | 21 | 28 | 31 | 28 | 41 | 27 |
| 12 | 27 | 22 | 27 | 32 | 28 | 42 | 27 |

EXAMPLE 2

Figure 11:
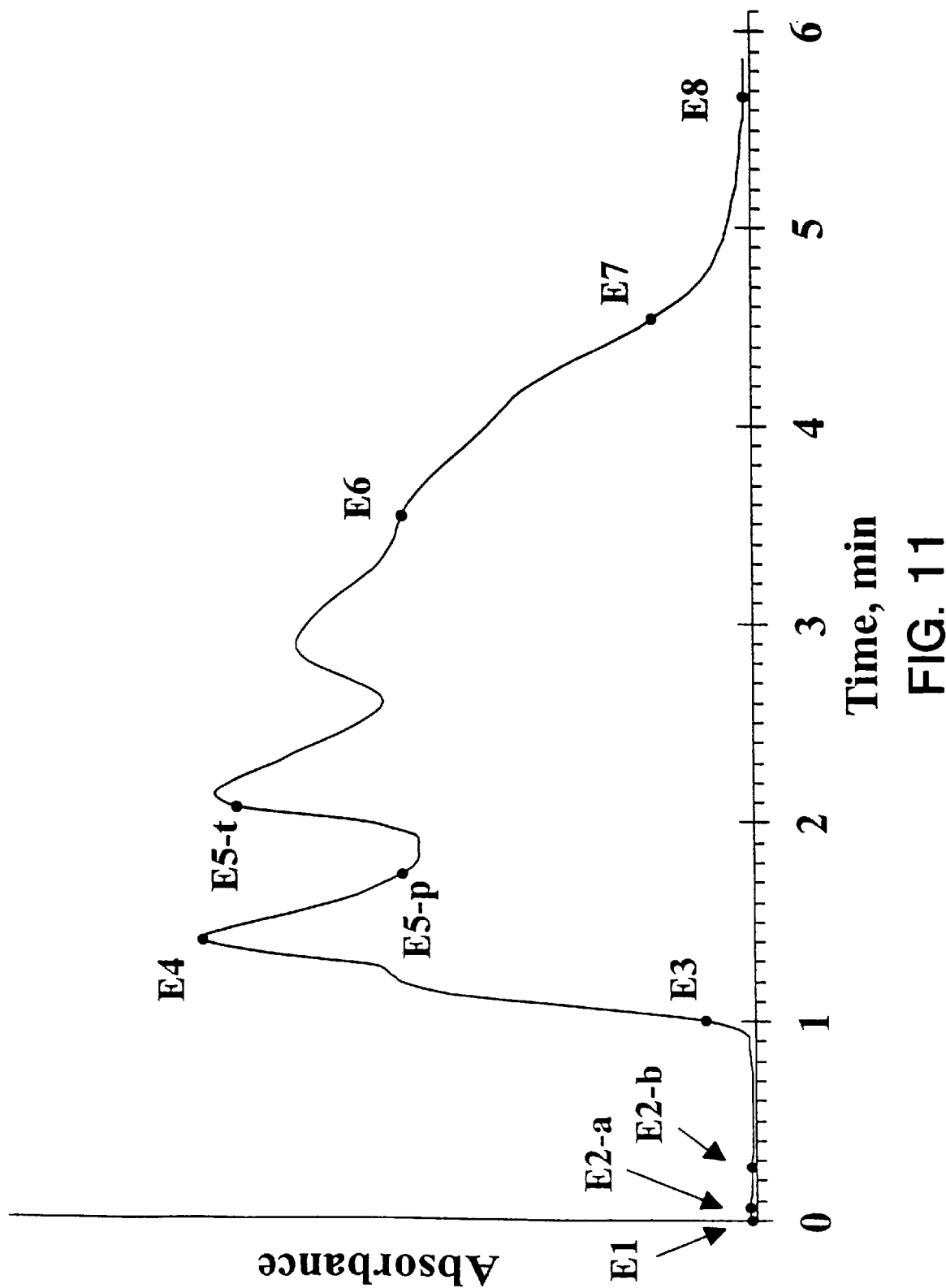
FIG. 11 is the chromatogram of Cycle 13 of Example 2.

This example, a run of 14 cycles, used the preferred embodiment depicted in FIG. 2. The cycle time was set at 6.0 min. The nominal flow rate of the Eldex injection pump 16 was set at 20 mL/min. Each injection occurred for 0.16 minute giving an injection volume of 3.2 mL. Thus 96 mg each of methyl and propyl p-hydroxybenzoate were injected each time. The other operating conditions are those given for Example 1. Event 2-3, the initiation of collection of Fraction 1, was triggered by the detection of the rising slope of the chromatographic profile. Specifically, valve 7 was opened and valve 11 was closed when a rising slope equal to 20% of the maximum detector signal per second was detected by the software. Events 2-4 through 2-8 were each triggered at set amounts of time after the initiation of Event 2-3. FIG. 11 shows the chromatogram for Cycle 13. The eight events discussed above are labeled in FIG. 3 as follows:

E1 indicates Event 2-1: The injection valve 12 was placed in load position, indicated by the solid-line flow path in FIG. 1. The waste valve 11 was opened. This event occurred at 0.0 minutes in the cycle.

E2-a indicates the beginning of Event 2-2: The injection pump 16 was switched on to fill the injection loop 13. This event occurred at 0.10 minutes in the cycle.

E2-b indicates the end of Event 2-2: The injection pump 16 was switched off, the injection loop 13 having been filled. This event occurred at 0.26 minutes in the cycle.

E3 indicates Event 2-3: Valve 7 was opened to begin collection of Fraction 1, methyl p-hydroxybenzoate. This occurred when a rising slope equal to 20% of the maximum detector signal per second was detected by the software. As shown in Table 2, this event occurred at about 62 seconds or about 1.03 minutes in the cycle.

E4 indicates Event 2-4: Valve 7 was closed to stop collection of Fraction 1. The recycle valve 6 was opened to allow the unresolved chromatographic profile to recycled onto the column 3 via the solvent pump 2. This event occurred 0.4 minutes after initiation of Event 2-3 or about 1.43 minutes in the cycle.

E5-p and E5-t indicate Event 2-5: The injection valve 12 was switched to the inject position, indicated by the solid-line flow path in FIG. 1. The interior of the chromatographic profile was thus diverted to travel through the injection loop 13. This resulted in 3.2 mL of fresh sample, 96 mg of methyl p-hydroxybenzoate and 96 mg of propyl p-hydroxybenzoate, being injected into the interior of the chromatographic profile. E5-t indicates the time at which this event occurred, 1.04 minutes after initiation of Event 2-3 or about 2.07 minutes in the cycle. Because the profile traveled through the solvent pump 2 (approximate volume=7 mL) before reaching the injection loop 13, the point on the profile at which sample was actually injected passed through the detector about 0.35 minutes earlier (7 mL/[20 mL/min]). E5-p indicates, therefore, the point on the profile where the injection of fresh sample actually occurred. E5-p therefore occurred approximately 0.69 minutes after initiation of Event 2-3 or about 1.72 minutes in the cycle. In subsequent chromatograms for this example, the beginning of Event 2-6 will be indicated by E5-p.

E6 indicates Event 2-6: The recycle valve 6 was closed and valve 9 was opened to begin collection of Fraction 2. This event occurred, 2.55 minutes after initiation of Event 2-3 or about 3.58 minutes in the cycle.

E7 indicates Event 2-7: The collection valve 9 was closed and collection valve 10 was opened to begin collection of Fraction 3. This event occurred 3.55 minutes after initiation of Event 2-3 or about 4.58 minutes in the cycle.

E8 indicates Event 2-8: The solvent pump 2 was shut off until the end of the cycle. This event occurred 4.67 minutes after initiation of Event 2-3 or about 5.70 minutes in the cycle. Thus the solvent pump was shut off approximately 0.30 minutes or 18.0 seconds at the end of each cycle. This result implies that the true cycle time, i.e. the circulation time of the chromatographic profile, is approximately 5.70 minutes under the conditions of temperature, flow rate, and mobile phase composition used for this run. Thus this run could have been duplicated by entering directly into the control software this value of the cycle time (5.70 minutes) and the absolute times for each event as determined above (0.0 minutes for E1, 0.10 minutes for E2-a, 0.26 minutes for E2-b, 1.03 minutes for E3, 1.43 minutes for E4, 2.07 for E5-t, 3.58 minutes for E6, and 4.58 minutes for E7). E8 would not have been employed if this direct approach had been used.

Figure 12:
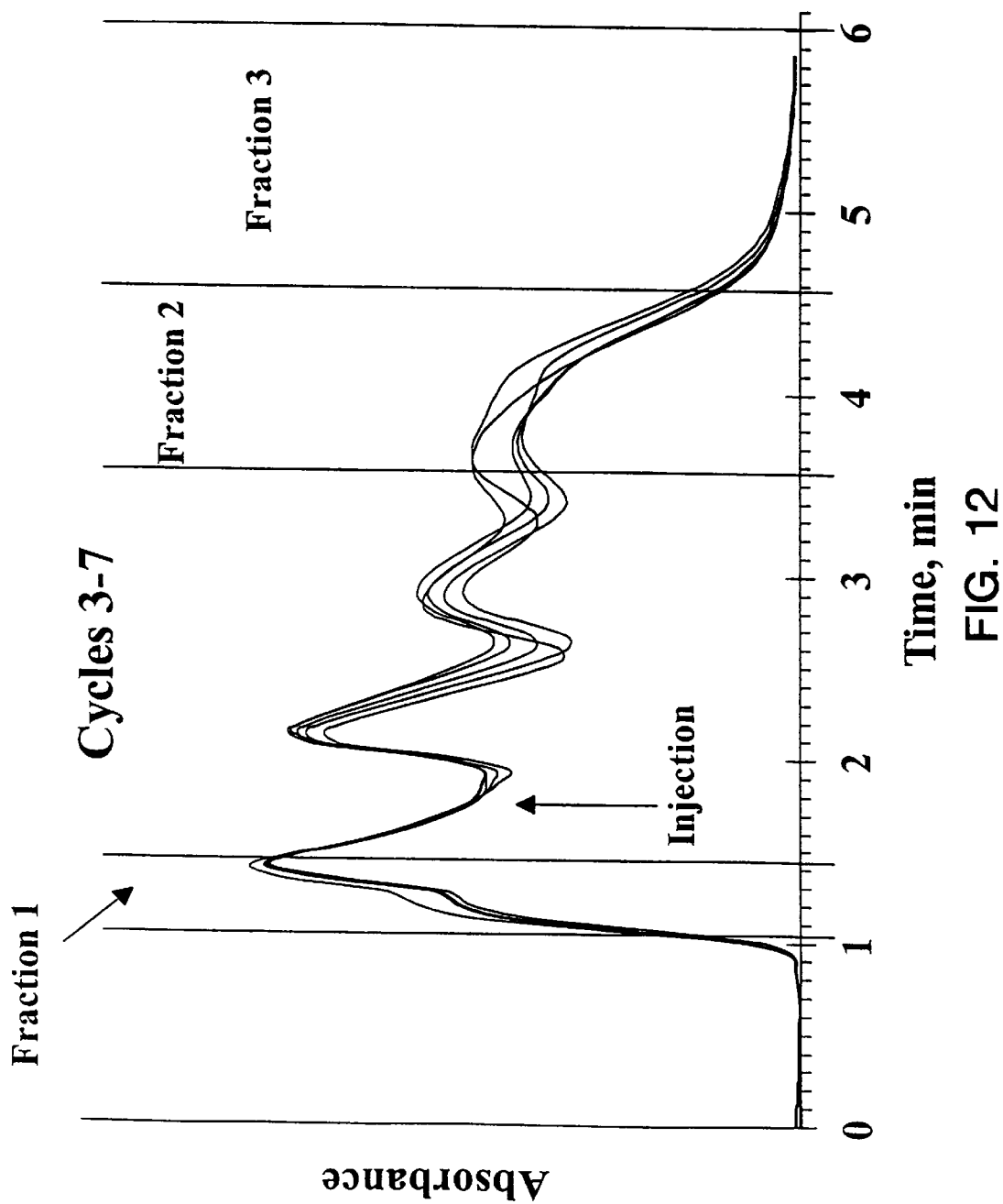
FIG. 12 is the superimposed chromatograms of Cycles 3–7 of Example 2.
Figure 13:
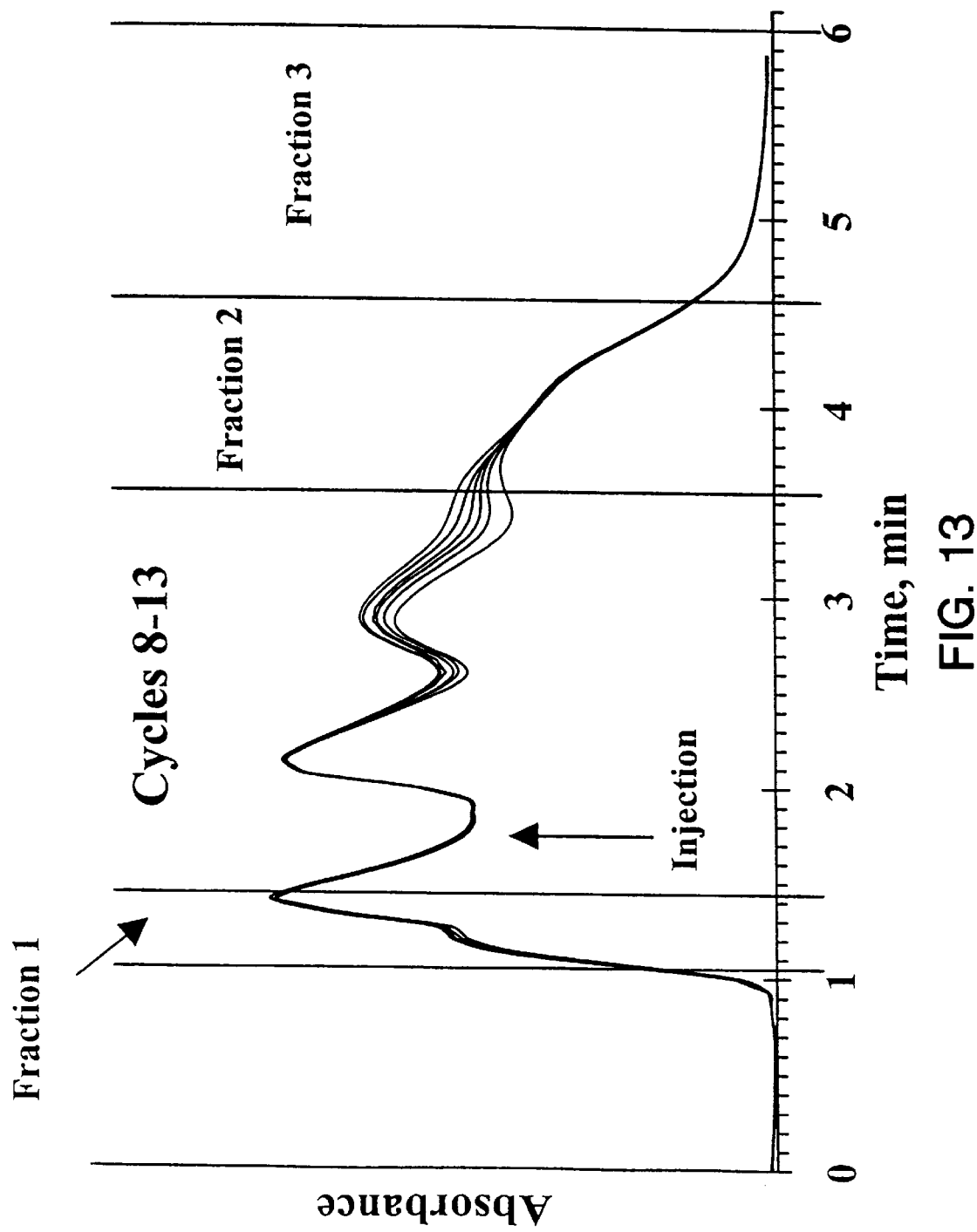
FIG. 13 is the superimposed chromatograms of Cycles 8–13 of Example 2.

FIG. 12 shows the superimposed chromatograms of Cycles 3–7, and FIG. 13 shows the superimposed chromatograms for Cycles 8–13. The leading part of the chromatographic profile, through the collection of Fraction 1, reached steady state by Cycle 4. The second half of the profile does not appear to have reached steady state by Cycle 14. Apparently, as with Example 1, several more cycles would have been required for the establishment of steady state.

Table 2 shows the times for each cycle at which Event 2-3, the initiation of collection of Fraction 1, occurred. These times are a measure of the reproducibility of the cycles on a time basis. As shown, the reproducibility of Event 2-3 is very good. Since all events subsequent to Event 2-3 occurred at set amounts of time after Event 2-3, all event times showed excellent reproducibility from cycle to cycle.

TABLE 2

Time of Initiation of Event 2–3 for Each Cycle

| Cycle | Time, sec. | Cycle | Time, sec. |
|---|---|---|---|
| 3 | 62 | 9 | 62 |
| 4 | 62 | 10 | 62 |
| 5 | 62 | 11 | 62 |
| 6 | 62 | 12 | 62 |
| 7 | 63 | 13 | 62 |
| 8 | 62 | 14 | 62 |

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A preparative chromatographic closed loop steady state cyclical process utilizing a single column comprising, at steady state conducting the following steps:

a. establishing and maintaining a circulating chromatographic profile through said column and through one solvent pump;

b. discontinuously and at each cycle injecting a sample comprising at least two components, into the interior of said maintained circulating profile of said single column, said injecting being conducted by an injection loop controlled in an inject position by an injection valve so as to inject the sample in the loop into the interior of said circulating profile, said injection valve remaining in the inject position from the time of injection until all of the profile has eluted from the column, and then adjusting the injection valve to a load position to load the injection loop when all the profile is on the column, and c. collecting, discontinuously and periodically, at least two enriched fractions from said circulating profile.

2. A process according to claim 1, further comprising:

d. through the solvent pump, pumping solvent, as a mobile phase, substantially continuously into the column during a single cycle.

3. A process according to claim 2, further comprising for each steady state cycle:

e. referencing with respect to time all events that occur after the start of collection of a Fraction 1 to the event which comprises the start of said collection of Fraction 1;

f. stopping the solvent pump during the collection of a Fraction 3, such stoppage continuing until the end of the cycle thereby providing reproducible cycles with respect to time.

4. A process according to claim 1, wherein no loss of the circulating profile occurs during the injection onto said maintained circulating profile.

* * * * *